United States Patent
Mathur et al.

(10) Patent No.: US 11,406,937 B2
(45) Date of Patent: Aug. 9, 2022

(54) PHOTOCATALYTIC FILTRATION IN VEHICLE HVAC SYSTEM

(71) Applicant: Calsonic Kansei North America, Inc., Farmington Hills, MI (US)

(72) Inventors: Gursaran Das Mathur, Farmington Hills, MI (US); Silvia Denisse Vazquez Salazar, Farmington Hiils, MI (US); Scott Torok, Farmington Hills, MI (US)

(73) Assignee: CALSONIC KANSEI NORTH AMERICA, INC., Farmington Hills, MI (US)

( * ) Notice: Subject to any disclaimer, the term of this patent is extended or adjusted under 35 U.S.C. 154(b) by 63 days.

(21) Appl. No.: 16/414,967

(22) Filed: May 17, 2019

(65) Prior Publication Data
US 2020/0360858 A1 Nov. 19, 2020

(51) Int. Cl.
*B01D 53/88* (2006.01)
*B01D 46/00* (2022.01)
(Continued)

(52) U.S. Cl.
CPC .............. *B01D 53/885* (2013.01); *A61L 9/00* (2013.01); *B01D 46/0028* (2013.01);
(Continued)

(58) Field of Classification Search
CPC .......... B60H 3/0658; B60H 2003/0675; B60H 203/0691; B60H 3/0085; B60H 3/0608;
(Continued)

(56) References Cited

U.S. PATENT DOCUMENTS 7,674,436 B1 * 3/2010 Feldman ................. A61L 9/205
422/121
9,498,555 B2 * 11/2016 Hingorani ............ B01D 46/522
(Continued)

FOREIGN PATENT DOCUMENTS

KR 20080079756 9/2008
KR 20150024012 3/2015
(Continued)

OTHER PUBLICATIONS

International Search Report & Written Opinion on PCT Application No. PCT/US2021/018818 dated Apr. 28, 2021.
(Continued)

*Primary Examiner* — Allen R. B. Schult
(74) *Attorney, Agent, or Firm* — Foley & Lardner LLP

(57) ABSTRACT

A photocatalyst filtration system for a vehicle includes a housing having an airflow path, and a filter configured to filter air flowing in the airflow path, the filter having a first photocatalyst and a second photocatalyst. The system further includes a first ultraviolet (UV) light source disposed proximate the filter and configured to energize the first photocatalyst, and a second UV light source disposed proximate the filter and configured to produce light having a shorter wavelength than light produced by the first UV light source, and configured to energize the second photocatalyst. One of the first photocatalyst or the second photocatalyst is configured to remove odor from the air. The other of the first photocatalyst or the second photocatalyst is configured to remove bacteria from the air.

15 Claims, 3 Drawing Sheets

(51) Int. Cl.
*B01D 53/00* (2006.01)
*B60H 3/00* (2006.01)
*B60H 3/06* (2006.01)
*A61L 9/00* (2006.01)

(52) U.S. Cl.
CPC ....... *B01D 46/0038* (2013.01); *B01D 53/007* (2013.01); *B60H 3/0085* (2013.01); *B60H 3/0608* (2013.01); *B01D 2255/802* (2013.01); *B01D 2257/708* (2013.01); *B01D 2257/90* (2013.01); *B01D 2257/91* (2013.01); *B01D 2259/804* (2013.01); *B01D 2279/50* (2013.01); *B60H 3/0658* (2013.01); *B60H 2003/0675* (2013.01); *B60H 2003/0691* (2013.01)

(58) Field of Classification Search
CPC ..... B60H 2003/0691; A61L 9/00; A61L 9/20; A61L 9/205
USPC .......................................................... 96/224

See application file for complete search history.

(56) References Cited

U.S. PATENT DOCUMENTS

| 2006/0057020 | A1* | 3/2006 | Tufo ........................ F24F 3/16 422/24 |
| 2006/0127288 | A1 | 6/2006 | Hay et al. |
| 2007/0243114 | A1 | 10/2007 | Morrow et al. |
| 2016/0325606 | A1 | 11/2016 | Kim et al. |
| 2017/0036516 | A1 | 2/2017 | Kim et al. |
| 2018/0264162 | A1 | 9/2018 | Kim et al. |
| 2019/0240370 | A1* | 8/2019 | Benedek ................. A61L 9/122 |

FOREIGN PATENT DOCUMENTS

| KR | 20160036853 | 4/2016 |
| KR | 102027031 | 11/2019 |
| WO | WO-96/37281 | 11/1996 |
| WO | WO-2017/055094 | 4/2017 |
| WO | WO-2018/097560 | 5/2018 |

OTHER PUBLICATIONS

International Search Report re PCT/US2020/032959 dated Sep. 2, 2020.

* cited by examiner

PHOTOCATALYTIC FILTRATION IN VEHICLE HVAC SYSTEM

BACKGROUND

The present application relates generally to the field of air filtration in vehicle heating, ventilation, and air conditioning ("HVAC") systems and more specifically to using different types of ultraviolet light and filters to remove contaminants from air.

Currently, vehicles such as automobiles are regularly driven by a driver without any passengers and the vehicle sits unoccupied when the driver reaches his or her desired destination. However, as ridesharing increases and self-driving capabilities improve, it is expected that each vehicle is more likely to begin carrying multiple passengers at a time as well as throughout the day. The increase in the number and frequency of riders will also result in the increase in the number of contaminants (e.g., viruses, odors, particulate matter, etc.) entering the vehicle, which presents a danger of transmitting the contaminants between the occupants. Moreover, due to the confined space of an automobile, when compared to mass transit alternatives (e.g., buses, trains, etc.), air containing contaminants provided by one occupant is more likely to be recirculated by a vehicle HVAC system throughout the cabin and to the other occupants.

It is therefore advantageous to provide a vehicle HVAC system, which removes more contaminants from air recirculated in the vehicle.

SUMMARY

One embodiment relates to a filtration system for a vehicle, including a housing having an airflow path, and a filter disposed in the housing and configured to filter air flowing in the airflow path, the filter having a first photocatalyst and a second photocatalyst. The system further includes a first ultraviolet (UV) light source comprising a plurality of UV-A lightbulbs disposed proximate the filter and configured to energize the first photocatalyst, and a second UV light source comprising a plurality of UV-C lightbulbs disposed proximate the filter and configured to produce light having a shorter wavelength than light produced by the first UV light source, and configured to energize the second photocatalyst. The UV-A lightbulbs and the UV-C lightbulbs are arranged in alternating fashion in a lateral direction across the housing. One of the first photocatalyst or the second photocatalyst is configured to remove odor from the air. The other of the first photocatalyst or the second photocatalyst is configured to remove bacteria from the air.

Another embodiment relates to an HVAC system for a vehicle, including a housing, an evaporator disposed in the housing, and a filter having a filter upstream surface and an opposing filter downstream surface, the filter disposed in the housing upstream from the evaporator. The system further includes a plurality of UV lightbulbs disposed in the housing upstream and offset from the filter and configured to provide UV-A light and UV-C light to substantially the entire filter upstream surface.

DETAILED DESCRIPTION

Figure 1:
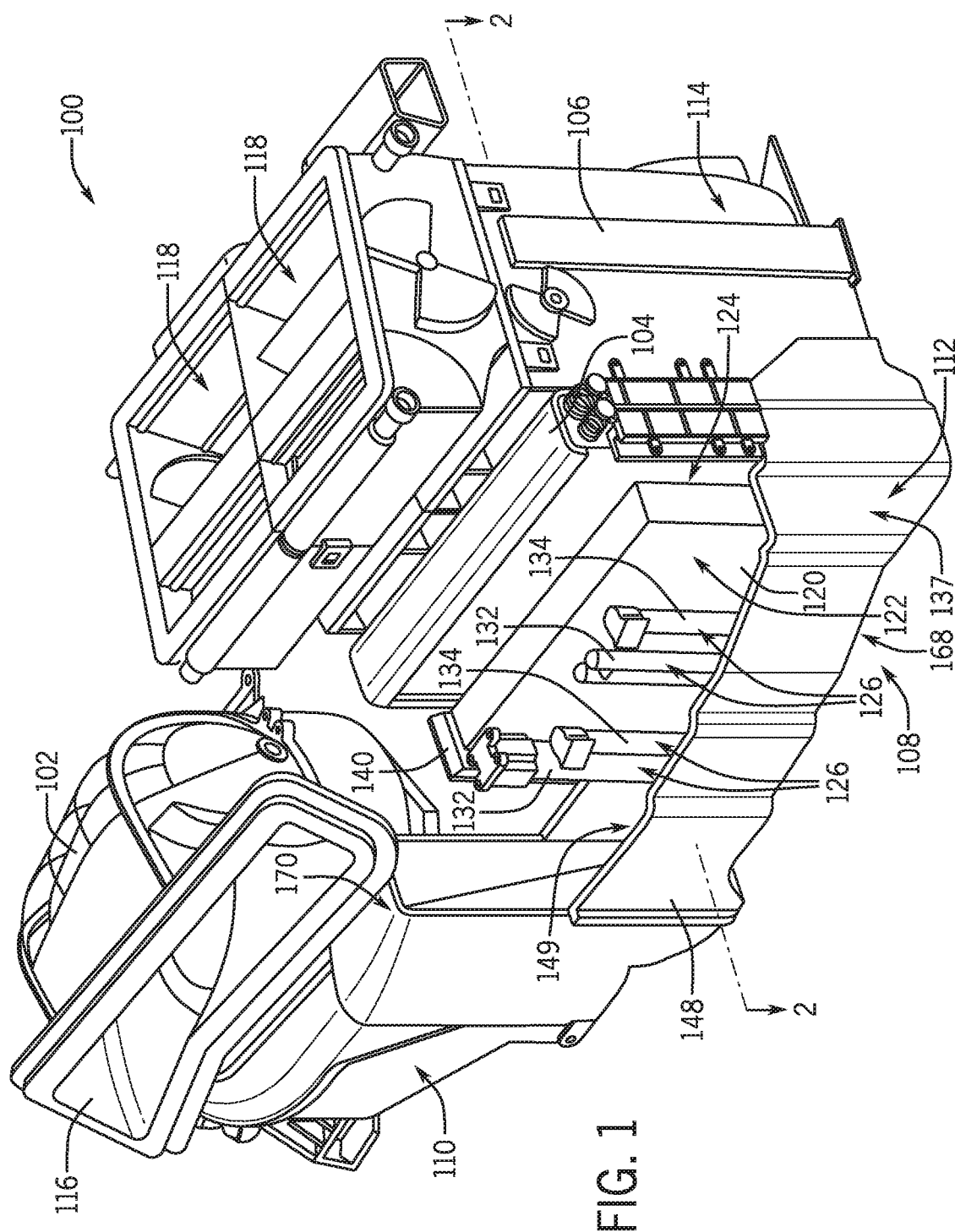
FIG. 1 is an HVAC system with photocatalytic filtration according to an exemplary embodiment.

Referring to FIG. 1, an HVAC system 100 is shown according to an exemplary embodiment. The HVAC system 100 includes a blower 102, an evaporator 104 downstream from the blower 102, and a heater 106 (shown in FIG. 2) downstream from the evaporator 104. The blower 102, evaporator 104, and heater 106 are disposed in a housing 108 and define an airflow path flowing therethrough. For example, the housing 108 may include a blower housing 110 containing the blower 102 therein, an evaporator housing 112 containing the evaporator 104 therein, and a heater housing 114 containing the heater 106 therein. An HVAC inlet 116 is formed at an upstream end of the housing 108 (e.g., at an upstream end of the blower housing 110) and is configured to supply air to the blower 102. An HVAC outlet 118 is formed at a downstream end of the housing 108 (e.g., at a downstream end of the heater housing 114) and is configured to output heated or cooled air from the HVAC system 100 to one or more portions of a passenger compartment of a vehicle.

The HVAC system 100 further includes a filter 120 disposed in the housing 108. For example, as shown in FIG. 1, the filter 120 is disposed in the evaporator housing 112 upstream from both the evaporator 104 and the heater 106. The filter 120 is shown downstream from the blower 102, although it should be understood that the filter 120 may be placed in other locations within or outside of the housing 108, such that the filter 120 is upstream from both the evaporator 104 and the heater 106. In this configuration, substantially all of the air received in the blower 102 and passed through the HVAC system 100 is required to flow through the filter 120, ensuring complete and efficient filtration of the air recirculating in a vehicle. According to other exemplary embodiments, in some configurations, air may pass downstream from the filter 120 directly to the heater 106, bypassing the evaporator 104. In this configuration, substantially all of the air still passes through the filter 120 first, before passing through the heater 106.

A plurality of ultraviolet (UV) lightbulbs 126 (i.e., lamps) are disposed in the housing 108, proximate and upstream from the filter 120. For example, the filter 120 defines a filter upstream surface 122 (i.e., an upstream end, a filter first end, etc.) and an opposing filter downstream surface 124 (i.e., a downstream end, a filter second end, etc.) and the plurality of UV lightbulbs 126 are disposed proximate the filter upstream surface 122. In this configuration, the UV lightbulbs 126 are disposed in the evaporator housing 112, although according to other exemplary embodiments, the UV lightbulbs 126 may be disposed in other locations within or outside of the housing 108, such that the UV lightbulbs 126 are upstream from the filter 120. According to another exemplary embodiment, the UV lightbulbs 126 may be disposed downstream from the filter 120, proximate the filter downstream surface 124 and upstream from the evaporator 104. According to yet another exemplary embodiment, the plurality of UV lightbulbs 126 may include at least one UV lightbulb 126 upstream from the filter 120 and at least one UV lightbulb 126 downstream from the filter 120.

It should be appreciated that the filter 120 and the UV lightbulbs 126 are positioned in the housing 108 upstream from the evaporator 104. Specifically, when the evaporator 104 operates in the HVAC system 100 in order to cool down the air passing through the evaporator 104, water condensation forms on the surface of the evaporator 104 and increases the humidity in the air output from and passing downstream from the evaporator 104 and into the passenger compartment of the vehicle. If the UV lightbulbs 126 were disposed close to or downstream from the evaporator 104, condensation could form on the UV lightbulbs 126, which would redirect portions of the UV light passing through the condensation and could result in portions of the filter 120 that is not directly contacted by UV light output from the UV lightbulbs 126, thereby reducing the effectiveness of the photocatalytic filtration through the filter 120.

Figure 2:
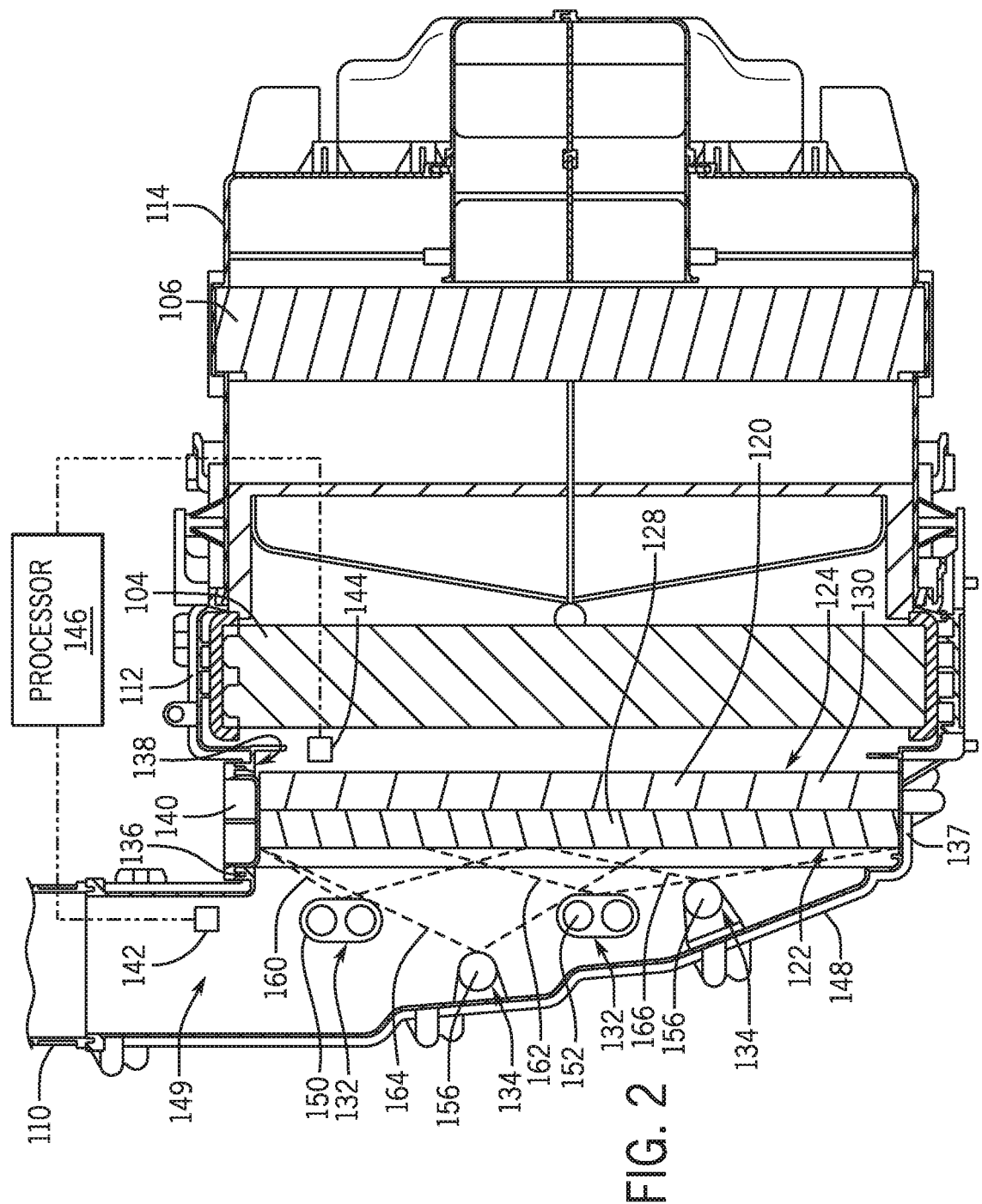
FIG. 2 is a cross-sectional view of a portion of the HVAC system showing the arrangement of ultraviolet lights and a filter.

Referring now to FIG. 2, a cross-section view of a portion of the HVAC system 100 is shown according to an exemplary embodiment. Specifically, the evaporator housing 112 and the heater housing 114 are shown with the filter 120 and the plurality of UV lightbulbs 126 disposed upstream from the evaporator 104 and the heater 106. The filter 120 may be a two-part filter, including both a titanium oxide (e.g., titanium dioxide or $TiO_2$) and carbon, and is configured to kill and remove viruses, bacteria, and volatile organic compounds (VOCs), such as odors, mold, or mildew from the air circulating in the vehicle. For example, FIG. 2 shows the filter 120 having a first layer 128 (i.e., titanium oxide layer, upstream layer, VOC layer, etc.) at or proximate the filter upstream surface 122, and a second layer 130 (i.e., substrate, downstream layer, carbon layer, high-efficiency particulate air or HEPA layer, etc.) at or proximate the filter downstream surface 124. The second layer 130 may serve as a substrate for the first layer 128, such that the first layer 128 is disposed directly on the second layer 130. In this configuration, the air passing through the filter 120 is received at the first layer 128 and then passes through the second layer 130 and is output from the filter downstream surface 124 to one or both of the evaporator 104 and the heater 106. According to other exemplary embodiments, the filter 120 may be integrally formed with both the carbon and $TiO_2$ being included as a single layer for filtering multiple types of particulates out of an air stream.

According to an exemplary embodiment, the first layer 128 includes a first photocatalyst, such as $TiO_2$. For example, the first layer 128 may include between approximately 0.1 and 0.5 $g/m^2$ of $TiO_2$ across substantially an entire surface area of the first layer 128 (e.g., at the filter upstream surface 122). It should be appreciated that an increase in the mass of $TiO_2$ per unit area (i.e., surface area density) increases resistance through the first layer 128 and, therefore, if the power of the blower 102 increases, then the surface area density of $TiO_2$ in the first layer 128 may be increased. During operation of the HVAC system 100, the UV lightbulbs 126 output UV light, which interacts with the $TiO_2$ surface of the first layer 128 through a process known as photocatalysis to generate electrons on the surface of the first layer 128. The electrons on the surface of the first layer 128 interact with water ($H_2O$) molecules in the air, breaking the molecules up into hydroxyl (OH) radicals, which are highly reactive and short-lived forms of hydroxide ions ($OH^-$). The hydroxyl radicals then interact with viruses, bacteria, and VOCs, which are each carbon-based complex molecules, during which the radicals break the complex molecules down into water and carbon dioxide ($CO_2$) constituents.

According to an exemplary embodiment, the plurality of UV lightbulbs 126 includes at least one UV-A lightbulb 132 (e.g., a first UV light source) and at least one UV-C lightbulb 134 (e.g., a second UV light source). Each UV-A lightbulb 132 is configured to produce light having a wavelength of between approximately 315 nm and 420 nm. The UV-A lightbulbs 132 may be U-shaped or fluorescent lightbulbs or have other shapes or types of lightbulbs and are configured to output UV-A light. The UV-A lightbulbs 132 may have a power supply terminal at one of an upper end or a lower end for providing power thereto. Each UV-C lightbulb 134 is configured to produce light having a wavelength of between approximately 100 nm and 280 nm. According to an exemplary embodiment, the UV lightbulbs 126 operate at approximately 12V and 100 W, with a heat flux of between approximately 30 $W/m^2$ and 40 $W/m^2$. FIGS. 1 and 2 show two (e.g., a plurality, a pair, etc.) UV-A lightbulbs 132 and two UV-C lightbulbs 134, although it should be appreciated that more or fewer UV-A lightbulbs 132 and/or UV-C lightbulbs 134 may be included in the HVAC system 100 upstream from the filter 120 or in other portions of the HVAC system 100.

According to an exemplary embodiment, the UV-A lightbulbs 132 are configured to transmit UV-A light to the first photocatalyst, which forms a portion of the first layer 128 to reduce or eliminate VOCs from the air. Specifically, UV-A light energizes the first photocatalyst as described above, to generate the hydroxyl radicals. The UV-A lightbulbs 132 are configured to break down the VOCs upstream from the second layer 130 (e.g., in the first layer 128 or upstream from the first layer 128), such that at least a portion of the constituent parts of the VOCs do not interact with carbon in the second layer 130. After passing the air through the first layer 128 of the filter 120, the air output from the HVAC system 100 into the vehicle contains fewer or no VOCs, reducing or eliminating any odor within the vehicle. This configuration can also be used with a vehicle's air intake, such as with the HVAC inlet 116 configured to receive air from outside the vehicle. In this configuration, the HVAC system 100 prevents the introduction of VOCs into the vehicle in the first place.

Similar to the UV-A lightbulbs 132, the UV-C lightbulbs 134 are configured to transmit UV-C light to the first layer 128 to reduce or eliminate bacteria and/or viruses from the air. The first layer 128 further includes a second photocatalyst, which may be the same as or different from the first photocatalyst and is configured to be energized by UV-C light. Specifically, the interaction of the UV-C and the second photocatalyst in the first layer 128 generates hydroxyl radicals, which breaks down the bacteria and/or viruses into mostly water and carbon dioxide, killing and removing the bacteria and/or viruses from circulation and protecting occupants in the vehicle. Advantageously, when the HVAC system 100 is used in a vehicle with multiple occupants, by constantly recirculating the air through the HVAC system 100, the likelihood of transmitting a virus or bacteria between passengers can be reduced. In this situation, the HVAC system 100 may operate an entire time that the vehicle is occupied to most effectively remove contaminants from the air. Notably, the blower 102 continues cycling air through the HVAC system 100 and through the filter 120 activated by the UV lightbulbs 126, even if the evaporator 104 and/or the heater 106 are not operating to affect the temperature inside the vehicle. According to another exemplary embodiment, the filtration aspects of the HVAC system 100 may be selectively engaged based on a condition of an occupant (e.g., known disease symptoms) to operate the UV lightbulbs 126 to filter the air with the filter 120 using photocatalysis.

Further, the HVAC system 100 may be operated in the vehicle for a period of time between uses by two different passengers. The vehicle may be a ride sharing vehicle, an autonomous vehicle, or another high occupancy transportation system (e.g., a taxi, a bus, a train, an airplane, etc.). The passengers may be positioned within the vehicle to face one another, which can increase the risk of spreading germs and viruses (e.g., the flu). In one example, a first passenger (i.e., occupant) may depart the vehicle. Then, the HVAC system 100 operates to purify the air currently in the vehicle before a second passenger enters the vehicle, thereby protecting future occupants from viruses or bacteria of earlier passengers. The HVAC system 100 may operate for a pre-determined amount of time required to completely circulate the volume of the passenger compartment. For example, the HVAC system 100 may operate for approximately 10 minutes, 15 minutes, 30 minutes or any other amount of time before a passenger enters the vehicle. In some implementations, an operating time for the HVAC system 100 after an earlier passenger departs the vehicle may be optimized based on UV settings or other parameters for the HVAC system 100 such as UV heat flux, TiO2 loading, and air flow rate. Among other benefits, the UV light emitted from the HVAC system 100 (e.g., UV light at a wavelength within a range between 100 and 480 nm or any other suitable range) will kill bacteria, viruses, mold and other pathogens contained within the vehicle cabin. The UV light will also breakdown VOCs such as cigarette smoke.

Referring still to FIG. 2, at least a portion of the second layer 130 of the filter 120 is formed from carbon. The second layer 130 may be configured to interact with portions of VOCs that are not broken down by the UV-A lightbulbs 132 to reduce odor output from the HVAC system 100 and being recirculated in the vehicle. According to an exemplary embodiment, the second layer 130 may be configured to filter out particles that are approximately 0.3 microns or greater with approximately 99.97% efficiency.

It should be appreciated that over time, particulate may build up on one or both of the layers 128, 130 in the filter 120, reducing the surface area available for passing air therethrough. This particle buildup reduces the operational efficiency of the HVAC system 100, requiring higher blower 102 output for the same volume air flow. As shown in FIG. 2, a first side wall 136 (i.e., a side wall) of the housing 108 (e.g., in the evaporator housing 112) defines a filter opening 138 therein and the HVAC system 100 includes a filter cover 140 disposed in the filter opening 138 and holding the filter 120 in place while sealing the housing 108. The filter cover 140 may further seal against the filter 120 to prevent air from passing around the filter 120, in a space between the filter 120 and the filter cover 140, rather than through the filter 120. According to another exemplary embodiment, the filter 120 may include the first layer 128 and not include the second layer 130 in order to prevent the buildup of particulate within the filter 120 and only purify the air through photocatalysis.

The HVAC system 100 may further include a first sensor 142 (i.e., an upstream sensor) disposed in the housing 108 upstream from the filter 120 and a second sensor 144 (i.e., a downstream sensor) disposed in the housing 108 downstream from the filter 120. For example, the first sensor 142 may be disposed in the evaporator housing 112 proximate the filter upstream surface 122 and configured to measure a first pressure $P_1$ (i.e., an upstream pressure) or a volume flow rate of air at the filter upstream surface 122. The second sensor 144 may be disposed in the evaporator housing 112 proximate the filter downstream surface 124 and upstream from the evaporator 104. The second sensor 144 is configured to measure a second pressure $P_2$ (i.e., a downstream pressure) or a volume flow rate of air at the filter downstream surface 124. The first and second sensors 142, 144 are connected to a processor 146 and are configured to send a signal to the processor 146 indicating the first pressure $P_1$ and the second pressure $P_2$, respectively.

A pressure differential is defined as a difference between the second pressure $P_2$ and the first pressure $P_1$ and is configured to represent or measure an amount of particle buildup on one or both of the first or second layers 128, 130 of the filter 120. Notably, the processor 146 receives the first pressure $P_1$ and the second pressure $P_2$ from the first and second sensors 142, 144, respectively and calculates the pressure differential based on these measurements. When the filter 120 is first installed in the HVAC system 100, the pressure differential may be approximately zero or very small. As particulate matter builds up in the filter 120 the pressure differential increases. A pre-determined threshold pressure is provided to the processor 146 and when the pressure differential exceeds the threshold pressure, the processor 146 outputs a signal (e.g., a light indicator, a message, etc.) either wired or wirelessly to a user or maintenance professional that the filter 120 needs to be changed. A user may then remove the filter cover 140 from the housing 108 and withdraw the used filter 120 from the housing 108 through the filter opening 138, followed by inserting a new filter 120 through the filter opening 138 and resealing the housing 108 by covering and sealing the filter opening 138 with the filter cover 140. According to another exemplary embodiment, signal may be configured to illuminate after a pre-determined time period, indicating a need to change the filter 120.

Referring still to FIG. 2, the UV lightbulbs 126, shown as UV-A lightbulbs 132 and UV-C lightbulbs 134, are arranged according to an exemplary embodiment. The evaporator housing 112 includes the first side wall 136 and an opposing second side wall 137. The filter 120 and the evaporator 104 each extend laterally across the evaporator housing 112 from the first side wall 136 to the second side wall 137. The housing 108 further includes a forward wall 148 (i.e., a main wall) upstream from and opposing filter upstream surface 122, and extending from the second side wall 137 toward the blower housing 110. An air inlet 149 is formed in the first side wall 136, proximate an upstream end of the evaporator housing 112, between the forward wall 148 and the filter 120.

Figure 3:
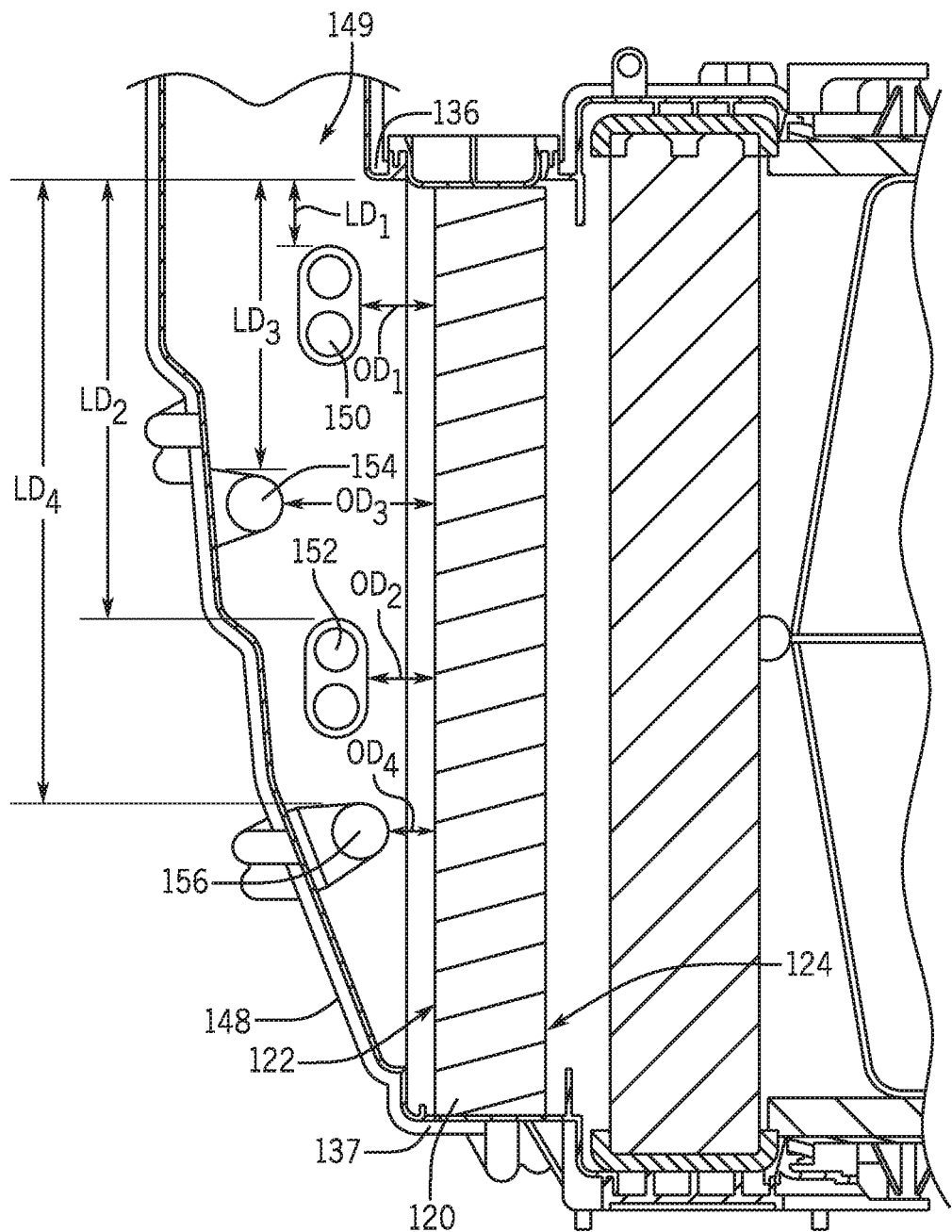
FIG. 3 is a portion of the cross-sectional view of FIG. 2, showing the placement of UV lightbulbs in the HVAC system.

The UV lightbulbs 126 extend substantially vertically and parallel to each other within the housing 108 as well as substantially parallel to the filter 120. Referring now to FIGS. 2 and 3, the UV lightbulbs 126 include a first lightbulb 150 and a second lightbulb 152 offset from the filter upstream surface 122 in a longitudinal direction, substantially perpendicular to the filter upstream surface 122. For example, the first lightbulb 150 is disposed a first offset distance $OD_1$ in the longitudinal direction, away from the filter upstream surface 122. Similarly, the second lightbulb 152 is disposed a second offset distance $OD_2$ in the longitudinal direction, away from the filter upstream surface 122. According to an exemplary embodiment, the first offset distance $OD_1$ and the second offset distance $OD_2$ may be substantially the same, such that the first UV lightbulb 150 is aligned with the second UV lightbulb 152 in a lateral direction, widthwise across the evaporator housing 112 between the first and second side walls 136, 137. According to another exemplary embodiment, the first offset distance $OD_1$ may be different from (e.g., greater or lesser than) the second offset distance $OD_2$.

Referring still to FIGS. 2 and 3, the first lightbulb 150 is disposed proximate and spaced apart from the first side wall 136 in the lateral direction (e.g., parallel to the filter upstream surface 122) by a first lateral distance $LD_1$. Similarly, the second lightbulb 152 is spaced apart from the first side wall 136 in the lateral direction by a second lateral distance $LD_2$, which is greater than the first lateral distance $LD_1$, such that the second lightbulb 152 is disposed closer to the second side wall 137 than the first lightbulb 150. It should be appreciated that the second lightbulb 152 is disposed proximate but spaced apart from the second side wall 137.

The UV lightbulbs 126 further include a third lightbulb 154 and a fourth lightbulb 156 offset from the filter upstream surface 122 in the longitudinal direction. As shown in FIG. 2, the third and fourth lightbulbs 154, 156 are disposed against the forward wall 148, although according to other exemplary embodiments, the forward wall 148 may have other arrangements, such that one or both of the third and fourth lightbulbs 154, 156 are spaced apart from the forward wall 148.

The third lightbulb 154 is disposed a third offset distance $OD_3$ in the longitudinal direction, away from the filter upstream surface 122. Similarly, the fourth lightbulb is disposed a fourth offset distance $OD_4$ in the longitudinal direction, away from the filter upstream surface 122. As shown in FIG. 2, the third offset distance $OD_3$ may be greater than one or both of the first offset distance $OD_1$ and the second offset distance $OD_2$, such that the third lightbulb 154 is disposed further away from the filter upstream surface 122 than one or both of the first and second lightbulbs 150, 152. The fourth offset distance $OD_4$ may be less than one or both of the first offset distance $OD_1$ and the second offset distance $OD_2$, such that the fourth lightbulb 156 is disposed closer to the filter upstream surface 122 than one or both of the first and second lightbulbs 150, 152. Similarly, the fourth offset distance $OD_4$ is less than the third offset distance $OD_3$, such that the fourth lightbulb 156 is closer to the filter upstream surface 122 than the third lightbulb 154.

According to other exemplary embodiments, the third and fourth lightbulbs 154, 156 may be disposed in other positions relative to the first and second lightbulbs 150, 152. For example, the third offset distance $OD_3$ may be less than one or both of the first offset distance $OD_1$ and the second offset distance $OD_2$, such that the third lightbulb 154 is disposed closer to from the filter upstream surface 122 than one or both of the first and second lightbulbs 150, 152. Similarly, the fourth offset distance $OD_4$ may be greater than one or both of the first offset distance $OD_1$ and the second offset distance $OD_2$, such that the fourth lightbulb 156 is disposed further away from the filter upstream surface 122 than one or both of the first and second lightbulbs 150, 152.

The third lightbulb 154 is spaced apart from the first side wall 136 in the lateral direction (e.g., parallel to the filter upstream surface 122) by a third lateral distance $LD_3$. The third lateral distance $LD_3$ is greater than the first lateral distance $LD_1$ and less than the second lateral distance $LD_2$, such that the third lightbulb 154 is disposed laterally between the first and second lightbulbs 150, 152 and is configured to provide light between the first and second lightbulbs 150, 152 directly to the filter upstream surface 122. Similarly, the fourth lightbulb 156 is spaced apart from the first side wall 136 in the lateral direction by a fourth lateral distance $LD_4$, which is greater than the second lateral distance $LD_2$, such that the fourth lightbulb 156 is disposed laterally between the second lightbulb 152 and the second side wall 137. It should be appreciated that the second lightbulb 152 is disposed proximate but spaced apart from the second side wall 137. It should further be noted that in the configuration shown in FIG. 2, the UV lightbulbs 126 are shown alternating (i.e., arranged in an alternating fashion) between UV-A lightbulbs 132 and UV-C lightbulbs 134 in the lateral direction.

According to other exemplary embodiments, the third lateral distance $LD_3$ may be less than the first lateral distance $LD_1$, such that the third lightbulb 154 is disposed laterally between the first side wall 136 and the first lightbulb 150. Similarly, the fourth lateral distance $LD_4$ may be greater than the first lateral distance $LD_1$ and less than the second lateral distance $LD_2$, such that the fourth lightbulb 156 is disposed laterally between the first and second lightbulbs 150, 152 and is configured to provide light between the first and second lightbulbs 150, 152 directly to the filter upstream surface 122.

As shown in FIG. 2, the first lightbulb 150 emits UV-A light along a first light field 160 downstream toward the filter upstream surface 122. Similarly, the second lightbulb 152 emits UV-A light along a second light field 162 downstream toward the filter upstream surface 122. The first light field 160 extends directly to the filter upstream surface 122 at the first side wall 136 and at least partway toward the second side wall 137. The second light field 162 extends directly to the filter upstream surface 122 at the second side wall 137 and at least partway toward the first side wall 136, such that the first light field 160 and the second light field 162 overlap on at least a portion of the filter upstream surface 122. In this configuration, UV-A light is applied directly to substantially the entire filter upstream surface 122 without requiring reflection of the light within the housing 108. It should be appreciated that the fourth lightbulb 156 is positioned in the evaporator housing 112, such that the fourth lightbulb 156 is not between the second lightbulb 152 and the filter upstream surface 122 at the second side wall 137 and therefore does not interfere with providing UV-A light directly to the entire filter upstream surface 122.

Similar to the first and second lightbulbs 150, 152, the third lightbulb 154 emits UV-C light along a third light field 164 downstream toward the filter upstream surface 122 and the fourth lightbulb 156 emits UV-C light along a fourth light field 166 downstream toward the filter upstream surface 122. The third light field 164 extends directly to the filter upstream surface 122 at the first side wall 136 and at least partway toward the second side wall 137. The fourth light field 166 extends directly to the filter upstream surface 122 at the second side wall 137 and at least partway toward the first side wall 136, such that the third light field 164 and the fourth light field 166 overlap on at least a portion of the filter upstream surface 122. For example, the third light field 164 and the fourth light field 166 may overlap on a portion of the filter upstream surface 122 directly downstream from the second lightbulb 152.

In this configuration, UV-C light is applied directly to substantially the entire filter upstream surface 122 without requiring reflection within the housing 108. It should be appreciated that the second offset distance $OD_2$ is provided, such that second lightbulb 152 is positioned in the evaporator housing 112 far enough away from the filter upstream surface 122 to allow both the third light field 164 and the fourth light field 166 to overlap on the filter upstream surface 122. In other words, the second lightbulb 152 is not disposed between any portion of the filter upstream surface 122 and at least one of the third or fourth lightbulbs 154, 156. Similarly, the first offset distance $OD_1$ is provided, such that the first lightbulb 150 is positioned in the evaporator housing 112 far enough away from the filter upstream surface 122 to allow the third light field 164 to directly contact the filter upstream surface 122 at the first side wall 136. In other words, the first lightbulb 150 is not disposed between the third lightbulb 154 and the filter upstream surface 122 at the first side wall 136.

As provided in FIG. 2, it should be appreciated that due to the staggered arrangement of the UV lightbulbs 126, UV-A light is provided from at least one of the first or second lightbulbs 150, 152 directly to substantially the entire filter upstream surface 122 and UV-C light is provided from at least one of the third or fourth lightbulbs 154, 156 directly to substantially the entire filter upstream surface 122. While the first and second lightbulbs 150, 152 are shown as UV-A lightbulbs 132, it should be understood that according to other exemplary embodiments, one or both of the first and second lightbulbs 150, 152 may be UV-C lightbulbs 134, configured to output UV-C light. Further, while third and fourth lightbulbs 154, 156 are shown as UV-C lightbulbs 134, it should be understood that according to other exemplary embodiments, one or both of the third and fourth lightbulbs 154, 156 may be UV-A lightbulbs 132, configured to output UV-A light. According to yet other exemplary embodiments, one or more of the UV lightbulbs 126 may be configured to output a different wavelength of light.

Referring again to FIG. 1, the housing 108 is shown having a lower surface 168 (i.e., a lower wall) at a lower periphery of the forward wall 148 and an opposing upper surface 170 (i.e., an upper wall) at an upper periphery of the forward wall 148. It should be appreciated that a portion of the evaporator housing 112 is shown broken away to show the UV lightbulbs 126, the filter 120 and the evaporator 104, and that the upper surface 170 of the housing 108 includes a portion of the evaporator housing 112 between the blower housing 110 and the heater housing 114. According to an exemplary embodiment, at least one of the UV lightbulbs 126 may be inserted substantially vertically through one of the lower surface 168 or the upper surface 170 of the housing 108 into the heater housing 114. The UV lightbulbs 126 may then be coupled (i.e., fixed) to one or both of the lower surface 168 and/or the upper surface 170. In this configuration, the UV lightbulbs 126 may be accessible for replacement from outside the housing 108 without disassembling the housing 108. According to other exemplary embodiments, at least a portion of the evaporator housing 114 or other portion of the housing 108 may be removable to provide access to the UV lightbulbs 126. According to another exemplary embodiment, the UV lightbulbs 126 may be electrically coupled externally to the housing 108 to a power source.

Further, as shown in FIGS. 1 and 2, the UV lightbulbs 126 are shown in a substantially vertical orientation. However, it should be understood that according to other exemplary embodiments the UV lightbulbs 126 may be arranged in a substantially horizontal direction. In other words, the lateral direction may be defined height wise across the evaporator housing 112 between the lower surface 168 and the upper surface 170. In this configuration, the lateral distances (e.g., the first lateral distance $LD_1$, etc.) for each of the UV lightbulbs 126 may be measured relative to one of the lower surface 168 or the upper surface 170. In the horizontal orientation, the UV lightbulbs 126 are disposed substantially parallel to the lower surface 168 and/or the upper surface 170 and are substantially perpendicular to the first side wall 136 and the second side wall 137.

According to another exemplary embodiment, the UV lightbulbs 126 may be arranged in other orientations, such that the UV lightbulbs 126 are substantially parallel to each other and/or the filter upstream surface 122. According to yet another exemplary embodiment, the UV lightbulbs 126 may include more or fewer than two UV-A lightbulbs 132 and/or two UV-C lightbulbs 134, such that substantially the entire filter upstream surface 122 is exposed directly to both UV-A light and UV-C light.

While FIGS. 1 and 2 show the UV lightbulbs 126 disposed in the evaporator housing 112 upstream from the filter 120, according to another exemplary embodiment, one or more of the UV lightbulbs 126 may be disposed downstream from the filter 120. For example, the UV lightbulbs 126 may be disposed between the filter downstream surface 124 and the evaporator 104 and are configured to transmit UV-A and/or UV-C light directly to the filter downstream surface 124. In this configuration, the filter 120 may be arranged with the first layer 128 still disposed upstream from the second layer 130 or the filter 120 may be flipped, such that the first layer 128 is disposed downstream from the second layer 130, such that the UV lightbulbs 126 transmit UV light from downstream of the filter 120 to directly on the first layer 128 at the filter downstream surface 124. In this configuration, the offset distances (e.g., the first offset distance $OD_1$, etc.) for each of the UV lightbulbs 126 may be measured from the filter downstream surface 124 in the downstream longitudinal direction (e.g., perpendicular to the filter downstream surface 124).

According to yet another exemplary embodiment, UV lightbulbs 126 may be disposed both upstream from and downstream from the filter 120. For example, at least one UV-A lightbulb 132 (e.g., both UV-A lightbulbs 132) may be disposed upstream from the filter 120 and at least one UV-C lightbulb 134 (e.g., both UV-C lightbulbs 134) may be disposed downstream from the filter 120. Similarly, according to another exemplary embodiment, at least one UV-C lightbulb 134 (e.g., both UV-C lightbulbs 134) may be disposed upstream from the filter 120 and at least one UV-A lightbulb 132 (e.g., both UV-A lightbulbs 132) may be disposed downstream from the filter 120. According to yet another exemplary embodiment at least one UV-A lightbulb 132 and at least one UV-C lightbulb 134 may be disposed both upstream from and downstream from the filter 120, such that both UV-A and UV-C light is transmitted directly to both the filter upstream surface 122 and the filter downstream surface 124.

It should further be appreciated that the HVAC system 100 may be installed in vehicles with various types of powertrains. For example, the HVAC system 100 may be installed in an electric vehicle ("EV"), a hybrid-electric vehicle ("HEV"), a vehicle with an internal combustion engine ("ICE") with or without a start-stop feature, or other powertrains. Further, it should be appreciated that an existing HVAC system in a vehicle may be retrofit by installing the filter 120 and the UV lightbulbs 126 in the existing HVAC system in any of the configurations described in this application.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of this disclosure as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the position of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is to be understood that although the present invention has been described with regard to preferred embodiments thereof, various other embodiments and variants may occur to those skilled in the art, which are within the scope and spirit of the invention, and such other embodiments and variants are intended to be covered by corresponding claims. Those skilled in the art will readily appreciate that many modifications are possible (e.g., variations in sizes, dimensions, structures, shapes and proportions of the various elements, values of parameters, mounting arrangements, use of materials, colors, orientations, manufacturing processes, etc.) without materially departing from the novel teachings and advantages of the subject matter described herein. For example, the order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed is:

1. An HVAC system for a vehicle comprising:
 a housing;
 an evaporator disposed in the housing;
 a filter having a filter upstream surface and an opposing filter downstream surface, the filter disposed in the housing upstream from the evaporator, wherein the housing comprises:
  a forward wall opposing the filter;
  an upper surface formed at an upper periphery of the forward wall;
  a lower surface formed at a lower periphery of the forward wall; and
  an air inlet formed at a first side wall of the housing between the forward wall and the filter; and
 a plurality of UV lightbulbs disposed in the housing upstream and offset from the filter and configured to provide UV-A light and UV-C light to substantially the entire filter upstream surface, wherein a first lightbulb of the plurality of UV lightbulbs is disposed a first offset distance away from the filter and a second lightbulb of the plurality of UV lightbulbs is disposed a second offset distance away from the filter different from the first offset distance, wherein one of the first lightbulb or the second lightbulb is coupled to the forward wall and the other of the first lightbulb or the second lightbulb is coupled to at least one of the upper surface or the lower surface, wherein:
  the filter comprises a photocatalyst energized by the UV-A light and the UV-C light on the upstream surface;
  the UV-A light is emitted along a UV-A light field toward the filter upstream surface;
  the UV-C light is emitted along a UV-C light field toward the filter upstream surface; and
  the UV-A light field and the UV-C light field overlap.

2. The system of claim 1, wherein each of the plurality of UV lightbulbs are substantially parallel to each other and to the filter upstream surface.

3. The system of claim 1, wherein:
 the filter extends laterally in the housing between the first side wall and a second side wall;
 the first lightbulb is spaced apart laterally from the first side wall by a first lateral distance;
 the second lightbulb is spaced apart laterally from the first side wall by a second lateral distance greater than the first lateral distance; and
 the plurality of UV lightbulbs further comprises:
  a third lightbulb spaced apart laterally from the first side wall by a third lateral distance greater than the first lateral distance and less than the second lateral distance; and
  a fourth lightbulb spaced apart laterally from the first side wall by a fourth lateral distance greater than the second lateral distance.

4. The system of claim 3, wherein:
 the first and second lightbulbs are UV-A lightbulbs; and
 the third and fourth lightbulbs are UV-C lightbulbs.

5. The system of claim 3, wherein:
 substantially the entire filter upstream surface is configured to receive UV-A light directly from at least one of the first or second lightbulbs; and
 substantially the entire filter upstream surface is configured to receive UV-C light directly from at least one of the third or fourth lightbulbs.

6. The system of claim 3, wherein:
 the first lightbulb spaced apart longitudinally from the filter upstream surface by the first offset distance;
 the second lightbulb spaced apart longitudinally from the filter upstream surface by the second offset distance;
 the third lightbulb spaced apart longitudinally from the filter upstream surface by a third offset distance; and
 the fourth lightbulb spaced apart longitudinally from the filter upstream surface by a fourth offset distance.

7. The system of claim 6, wherein:
 the third offset distance is greater than the first offset distance; and
 the third lightbulb is configured to transmit UV light directly to the filter upstream surface at the first side wall.

8. The system of claim 7, wherein the first lightbulb is not disposed directly between the third lightbulb and the filter upstream surface at the first side wall.

9. The system of claim 6, wherein:
the fourth offset distance is less than the second offset distance; and
the second lightbulb is configured to transmit UV light directly to the filter upstream surface at the second side wall.

10. The system of claim 9, wherein the fourth lightbulb is not disposed directly between the second lightbulb and the filter upstream surface at the second side wall.

11. The system of claim 1, wherein the photocatalyst comprises:
a first photocatalyst configured to be energized by the UV-A light; and
a second photocatalyst configured to be energized by the UV-C light.

12. The system of claim 1, wherein the filter comprises:
a first layer including the photocatalyst and configured to remove at least one of bacteria or volatile organic compounds from air when it receives at least one of the UV-A light or the UV-C light; and
a second layer including carbon and configured to remove particulate from the air.

13. The system of claim 1, wherein the photocatalyst comprises between 0.1 and 0.5 $g/m^2$ of $TiO_2$, inclusive.

14. The system of claim 1, wherein the plurality of UV lightbulbs are disposed in staggered arrangement between an air inlet of the housing and the filter.

15. The system of claim 1, wherein the first lightbulb is coupled to the upper surface and the second lightbulb is coupled to the lower surface.

* * * * *